United States Patent [19]

Imaeda et al.

[11] Patent Number: 5,702,883
[45] Date of Patent: Dec. 30, 1997

[54] METHODS FOR DETECTION OF MUTAGENS USING LUMINESCENCE GENE

[75] Inventors: Takao Imaeda, Kasugai; Masana Hirai, Seto, both of Japan

[73] Assignee: Kabushiki Kaisha Toyota Chuo Kenkyusho, Aichi, Japan

[21] Appl. No.: 326,949

[22] Filed: Oct. 21, 1994

[30] Foreign Application Priority Data

Oct. 22, 1993 [JP] Japan ................................ 5-264894
Feb. 15, 1994 [JP] Japan ................................ 6-018452
Sep. 26, 1994 [JP] Japan ................................ 6-229659

[51] Int. Cl.$^6$ .............................. C12Q 1/68; C12Q 1/66; C07H 21/04
[52] U.S. Cl. ................... 435/4; 435/6; 435/8; 536/23.1; 536/23.2; 536/23.7
[58] Field of Search .................... 435/6, 4, 8, 252.3, 435/252.33; 536/23.1, 23.2, 23.7

[56] References Cited

U.S. PATENT DOCUMENTS 4,849,335  7/1989  Hofnung et al. ........................ 435/6

FOREIGN PATENT DOCUMENTS 0 370 813  5/1990  European Pat. Off. .
0 463 570  1/1992  European Pat. Off. .

OTHER PUBLICATIONS

Schauer, "Visualizing gene expression with luciferase fusions", Trends Biotech. 6: 23–27, 1988.
Shaw et al., "Working with bacterial bioluminescence", Plant Molec. Biol. Reporter, 5(1): 225–236, 1987.
Greener et al., "Promoters of the broad host range plasmid RK2: Analysis of transcription (initiation) in five species of Gram–negative bacteria", Genetics 130: 27–36, 1992.
Lee et al., "Bioluminescence detection system of mutagen using firefly luciferase genes introduced in Escherichia coli lysogenic strain", Anal. Chem. 64: 1755–1759, 1992.
Mutation Research, vol. 272, 1992, pp. 91–99, Yoshimitsu Oda, et al., "A Sensitive UMU Test System For The Detection Of Mutagenic Nitroarenes In Salmonella Typhimurium NM1011 Having A High Nitroreductase Activity".
Mutation Research, vol. 147, 1985, pp. 219–229, Yoshimitsu Oda, et al., "Evaluation Of The New System (UMU–Test) For The Detection Of Environmental Mutagens And Carcinogens".
Proc. Natl. Acad. Sci. USA, vol. 79, pp. 5971–5975, Oct. 1982, Philippe Quillardet, et al. "Sos Chromotest, A Direct Assay Of Induction Of An SOS Function In Escherichia coli K–12 To Measure Genotoxicity".

Primary Examiner—Jasemine C. Chambers
Assistant Examiner—Scott D. Priebe
Attorney, Agent, or Firm—Oblon, Spivak, McClelland, Maier & Neustadt, P.C.

[57] ABSTRACT

A method for detecting or quantitating a mutagenic substance in a sample includes culturing a host microorganism transformed with a recombinant gene comprising an SOS gene and genes expressing luciferase activity and optionally genes expressing an enzyme which catalyzes the production of a substrate for luciferase, positioned downstream of the SOS gene, in a medium to which the sample is added; and measuring a luminescence generated by expression of the gene expressing luciferase activity. The method is sensitive, accurate and non-time consuming; and gene systems used for said method, i.e., a recombinant gene comprising an SOS gene expressed when a DNA is damaged and a gene expressing luciferase activity positioned downstream of the SOS gene, and a host microorganism transformed with said recombinant gene. Preferably the recombinant gene further comprises a gene expressing an enzyme which catalyses the production of a substrate for the luciferase in the down stream of the SOS gene.

3 Claims, 11 Drawing Sheets

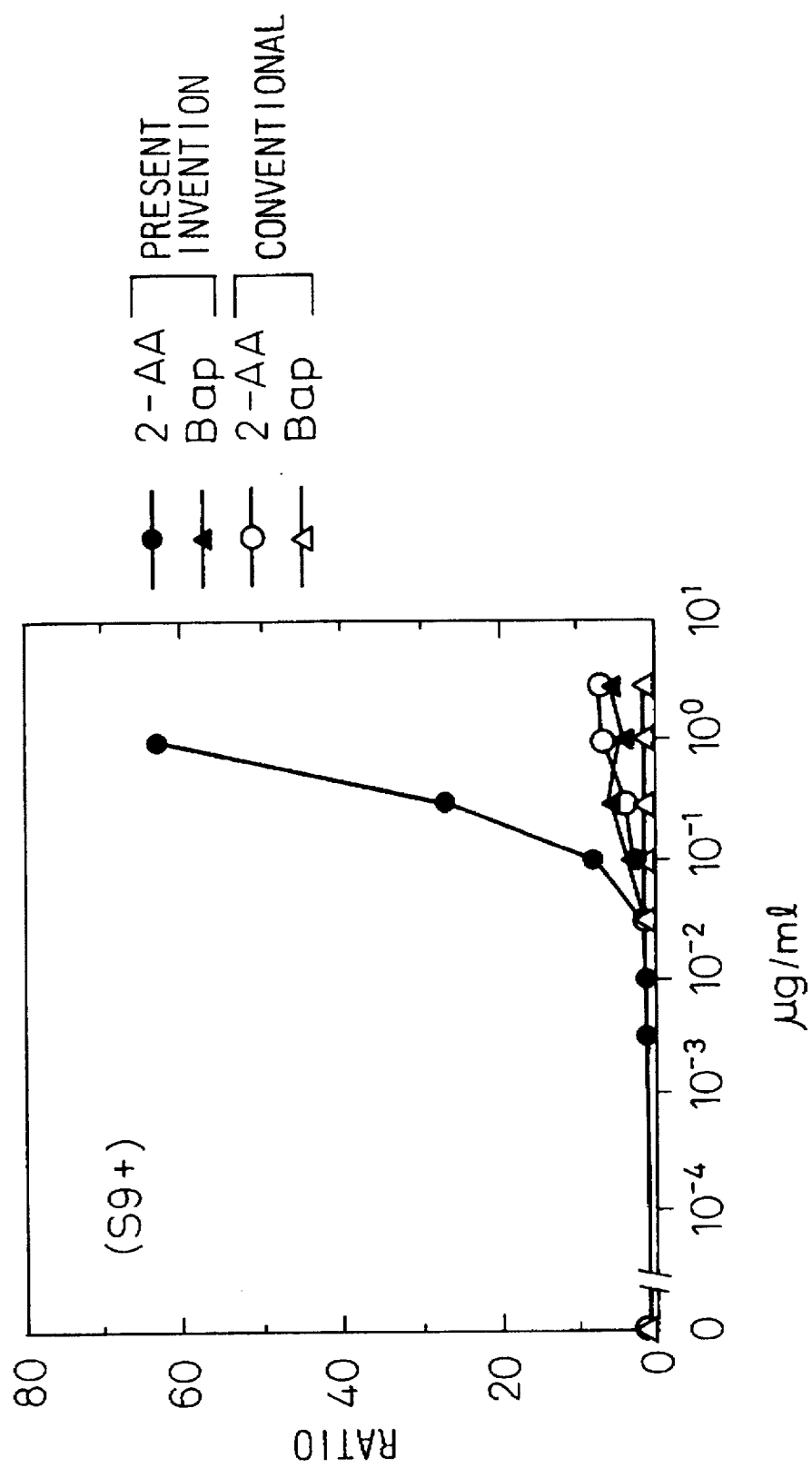

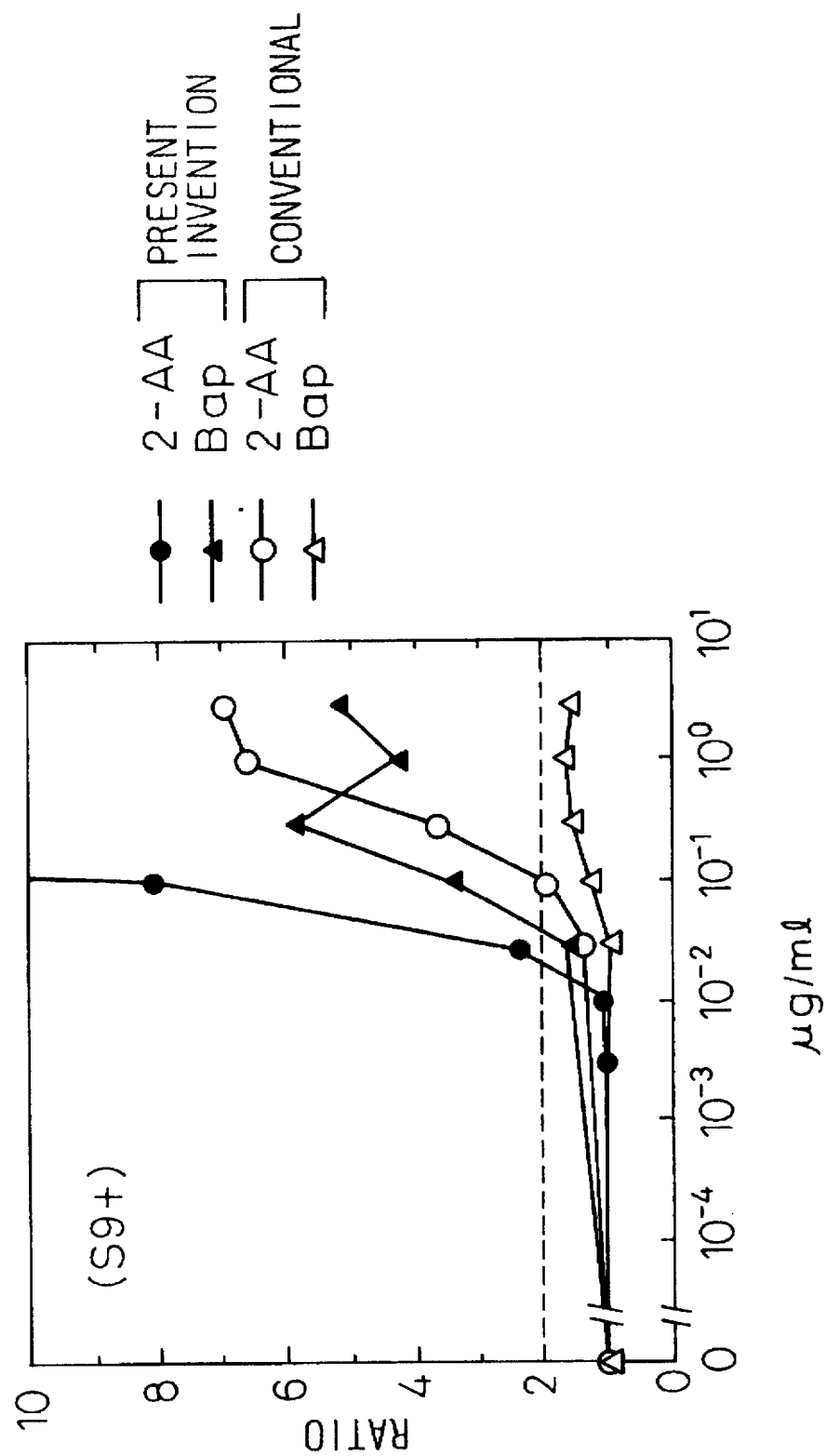

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc ="DNA linker"

( x i ) SEQUENCE DESCRIPTION: SEQ ID NO:1:

TAGGATCCTA  10

METHODS FOR DETECTION OF MUTAGENS USING LUMINESCENCE GENE

BACKGROUND OF THE INVENTION

1. Field of the Invention

The present invention relates to methods for detection of mutagenic substances using a luminescence gene. In one embodiment, the present method uses a luciferase gene, and in another embodiment the present method uses a luciferase gene and a gene expressing an enzyme catalyzing the production of a substrate for the luciferase.

2. Related Art

At present there are many reports relating to test methods using microorganisms for short term screening of carcinogens. Among them, Ames test using reverse mutation of a microorganism is widely used. However, this test method has drawbacks. For example, it takes about three days for completion of the test. Recently, short term methods (umu test and SOS chromo test) which detect damages to a DNA by genotoxic substances such as mutagenic substances different from Ames test which detects a mutation of a microbial cell were reported (Oda, Nakamura et al., "Evaluation of the new system (umu-test) for the detection of environmental mutagens and carcinogens", Mutation Research, 147, 219–229, 1985; Japanese Examined Patent Publication (Kokoku) 4-12118).

In these methods, an SOS response caused by DNA damage is measured as an amount of β-galactosidase expressed by lacZ gene positioned in the downstream of one of SOS genes i.e., umu D,C genes or sfiA gene, to detect damages to a DNA by genotoxic substances such as mutagenic substances.

More specifically, *Salmonella typhimurium* (umu test) or *E. coli* (SOS chromo test) introducing the above-mentioned gene is cultured in the presence of a substance to be tested, and the cells were disrupted by the addition of toluene or chloroform, and an aqueous solution of a sulfonate type surfactant such as sodium dodecylbenzene sulfonate, to the culture broth, if necessary after dilution with a buffer. Next, to measure β-galactosidase activity, an aqueous solution of a substrate for β-galactosidase, i.e., 2-nitrophenyl-β-D-galactopyranoside is added thereon, an enzyme reaction is carried out at 28° C., and some ten minutes later, the reaction is terminated with sodium carbonate. An optical density of the enzyme reaction mixture is measured at two wave lengths (420 and 550 nm), and a β-galactosidase activity is calculated according to Miller's method (Miller. J. H., Experiments in molecular genetics, Cold Spring Harbor Laboratory, 1972).

The above-mentioned umu test and SOS chromo test are characterized by simple and speedy detection in comparison with Ames test. However, sensitivity is low and it takes 7 to 8 hours for the detection. Especially, in these methods, sensitivity for detection of nitroarenes and polycyclic aromatic hydrocarbons is low. These methods include two steps of procedures for detection, i.e., the first step for inducing SOS response by culturing a host microorganism in the presence of a sample to be tested, and the second step for colorimetric detection of β-galactosidase expressed in microbial cells.

As specifically described above, the second step is more complicated than the first step in their operations, and needs various operations such as dilution, disruption of cells, addition of a substrate, proceeding and termination of coloring reaction, as well as measurement of optical absorption.

In addition, colorimetric detection is not advantageous because of its low sensitivity for detection. To increase the sensitivity of the detection, cells are disrupted so as to enhance the reactivity of intracellularly expressed β-galactosidase with externally added cell lysis reagents, and this operation makes the test further complicated.

As described above, those test methods based on colorimetric detection are disadvantageous in the following points: The second step requests complicated operations; detection sensitivity is low; and the addition of expensive colorimetric reagent is essential. In order to compensate the low sensitivity of the detection, it is necessary to prolong the time of coloring reaction and carry out complicated cell disruption treatment, whereby the speedy detection is spoiled.

Accordingly, in one embodiment of the present invention, a method for detection of genotoxic substances such as mutagenic substances using induction of SOS response is provided in which operations such as dilution, and proceeding and termination of coloring reaction are not necessary, and therefore operations are simplified, and detection speed, and detection sensitivity are improved. In another embodiment of the present invention, operations such as dilution, cell disruption treatment, proceeding and termination of coloring reaction, and the addition of substrate are not necessary, and therefore operations are remarkably simplified, and detection speed, detection sensitivity and economy are improved.

SUMMARY OF THE INVENTION

The present inventors, as a result of various researches to solve the above-mentioned drawbacks of the conventional methods, found that when a microorganism transformed with a recombinant gene in which a gene expressing a luciferase activity is positioned downstream of an SOS gene sensitive to a DNA damage is cultured in a medium containing a mutagenic substance, the gene expressing a luciferase activity is expressed simultaneously with the expression of said SOS gene, and a mutagenic substance can be detected or measured in a short time with high sensitivity by measuring the luminescence.

Accordingly, the present invention provides a recombinant gene comprising an SOS gene and a gene expressing luciferase activity positioned downstream of an SOS gene.

The present invention also provides a host microorganism transformed with the above-mentioned gene.

The present invention further provides a method for determining the presence or absence of a mutagenic substance, or measuring an amount of a mutagenic substance present, in a test sample, comprising the steps of culturing said microorganism in a medium containing a sample to be tested, and then measuring the luminescence by expression of gene expressing said luciferase activity.

In addition, the present inventor, as a result of various researches to solve the above-mentioned drawbacks of the conventional methods, found that when a microorganism transformed with a recombinant gene in which genes expressing luciferase activity and genes expressing an enzyme catalyzing the production of a substrate for the luciferase are positioned downstream of an SOS gene sensitive to a DNA damage is cultured in a medium containing a mutagenic substance, the genes expressing luciferase activity and an enzyme catalyzing the production of a substrate for the luciferase are expressed simultaneously with the expression of the SOS gene, and as a result, a condition for continuously and intracellularly providing the substrate for the luciferase activity resulting in luminescence by luciferase is established, and a genotoxic substances such as mutagenic substances can be detected or measured in a short time with high sensitivity by measuring said luminescence.

Accordingly, the present invention provides a recombinant gene comprising genes expressing luciferase activity and an enzyme catalyzing the production of a substrate for the luciferase positioned downstream of the SOS gene.

The present invention also provides a host microorganism transformed with the above-mentioned genes.

The present invention further provides a method for determining the presence or absence of a mutagenic substance, or measuring an amount of a mutagenic substance present, in a test sample, comprising the steps of culturing said microorganism in a medium containing a sample to be tested, and then measuring the luminescence by the expression of the genes expressing luciferase activity and an enzyme catalyzing the production of a substrate for the luciferase.

BRIEF EXPLANATION OF DRAWING

FIG. 10 is a graph showing ratio (0 to 80) obtained by dividing responses obtained in Example 6 and Comparative Example 4 for 2-AA and BaP at different concentrations, by response at sample-free condition.

FIG. 11 is a graph showing ratio (0 to 10) obtained by dividing responses obtained in Example 6 and Comparative Example 4 for 2-AA and BaP at different concentration, by response at sample-free condition.

DETAILED DESCRIPTION

Figure 1:
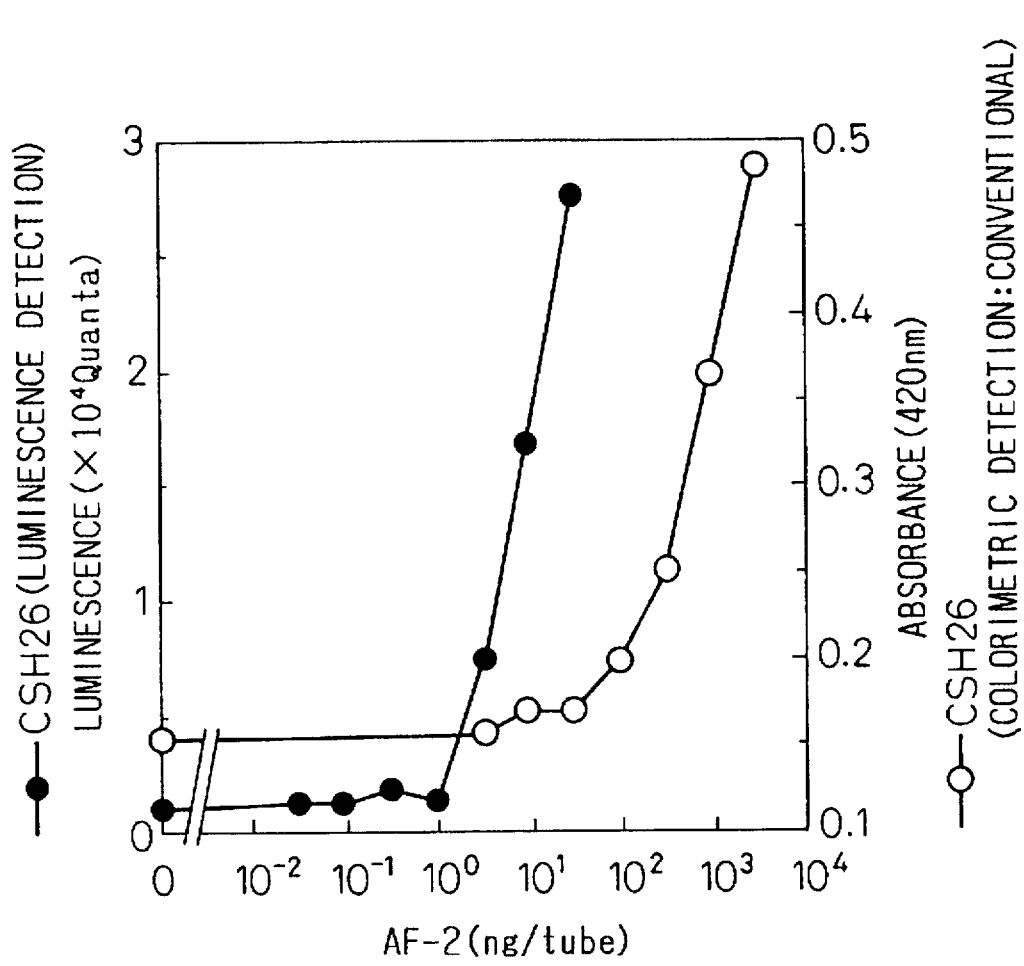
FIG. 1 shows a result of luminescence measurement method obtained in Example i (solid circles) and of colorimetric method obtained in Comparative Example 1 (open circles).

According to the present invention, to express a gene coding for luciferase activity, or genes coding for luciferase activity and an enzyme catalyzing the production of a substrate for luciferase, an SOS gene is used as a means for regulating the expression. Accordingly, the SOS gene may be any SOS gene which is expressed when a DNA is damaged and which contains so called SOS box. Accordingly, in the present invention, SOS gene expressed when a DNA is damaged is those containing the "SOS box". The SOS gene may be the SOS box per se, or DNA fragment containing the SOS box.

The SOS gene includes umu gene, such as umu D,C gene, as well as sfiA gene, but the SOS gene is not limited thereto. Among them umu D,C gene are described in Proc. Natl. Acad. Sci. USA Vol. 82, 4336–4340 (1985), and therefore can be easily obtained according to the description in the reference. In addition, plasmid pSK1002 containing umuD gene as well as a part of umuC gene and lacZ gene is described in H. Shinagawa et al., Gene, 23, 167 (1983), and from this plasmid, umu D,C gene can be easily obtained.

As a gene expressing a luciferase activity, various genes can be used. For example, a vector comprising luciferase gene (luc gene) derived from *Photinus pyralis* is commercially available from Toyo Ink MFG. Co., LTD. as Pica Gene™ as a cassette vector.

As genes expressing a luciferase activity or an enzyme catalyzing the production of a substrate for luciferase, any genes which express both the proteins under the control of SOS gene can be used. The genes include bioluminescence genes of marine bacteria, but are not limited thereto. Marine bacteria having the above defined bioluminescence genes include Vibrio group, the genus Vibrio, such as *Vibrio harveyi*, *V. fischeri*, *V. Splendidus*, *V. lendinus*, *V. cholerae*, and the genus Photobacterium, such as *P. phosphoreum*, *P. leiognathi* etc.

For example, bioluminescence genes derived from *V. ficsheri* are modified by removing operator region of the bioluminescence genes, remaining the structural gene region (genes expressing luciferase activity and genes expressing fatty acid reductase which is an enzyme catalyzing the production of aldehyde which is a substrate for luciferase) so as to make the bioluminescence genes easy to be used as a reporter gene. The modified gene is used to prepare cassette vectors. The cassette vectors such as pUCD320, pUCD613, pUCD614, pUCD618, pUCD620, pUCD623, pUCD1111 etc. have been reported. These vectors are further described in Clarence I. Kado et al., Plant Molecular Biology Reporter, 5, 225 (1987), and from these vectors, bioluminescence genes can be easily obtained.

Note, in the present invention, a substrate for luciferase is a long chain aldehyde or the like, and an enzyme catalyzing the production of said substrate is AND(P)H:FMN reductase, fatty acid reductases, or the like. In the above-mentioned examples, genes expressing a luciferase activity and genes expressing an enzyme catalyzing the production of a substrate for luciferase may be derived from the same source. However, these genes may be derived from different sources.

Host microorganism is any microorganism which allows SOS gene being expressed when a DNA is damaged by a genotoxic substance such as a mutagenetic substance, in other word, host microorganism may be those having the components of SOS response. For example, *Escherichia coli*, *Salmonella typhimurium* such as TA1535, TA1538, *Saccharomyces cerevisiae*, or the like, may be listed.

A recombinant gene comprising an SOS gene as well as genes for expressing a luciferase activity and an enzyme catalyzing the production of a substrate may be constructed by joining genes expressing luciferase activity and an enzyme catalyzing the production of a substrate for luciferase to the downstream of the SOS gene in a DNA fragment comprising at least a part of SOS box of SOS gene. Joining can be carried out according to a conventional procedure using DNA ligase. To introduce the recombinant DNA into a host microorganism, the recombinant DNA must be present in a vector. For example, as plasmids, pBR type plasmid, pUC type plasmid and the like may be used.

To transform a host microorganism with said expression vector, conventional procedures used for transformation of microorganisms such as bacteria may be used.

According to the present invention, a genotoxic substance such as a mutagenic substance is detected or measured by mixing a sample to be tested with a medium, and culturing said transformed host microorganism in said medium, usually for 1 to 3 hours.

According to the first embodiment of the present invention wherein the genes expressing an enzyme catalyzing the production of a substrate for luciferase is not used, the cultured microbial cells are collected, and the cell wall is disrupted to release an expression product, i.e., luciferase from the cells. The disruption of the cells can be carried out according to a conventional procedure, for example, the use of cell wall lysis reagent represented by a surfactant such as Triton X, Sodium Dodecyl Sulfate etc., or the mechanical treatment represented by sonication such as ultrasonication.

Next, the lysate thus obtained is, for example, centrifuged to obtain a supernatant containing luciferase, and the supernatant is subjected to a treatment for measuring luminescence. The measurement of luminescence is carried out by adding a substrate for luciferase such as luciferine and coenzymes to the supernatant.

According to another embodiment of the present invention wherein genes expressing an enzyme catalyzing the production of a substrate for luciferase is used, the cultured medium per se generates the luminescence if the sample contained a genotoxic substance such as a mutagenic substance. Therefore, immediately after the culturing the luminescence can be measured. Since an amount of the luminescence increases in a concentration dependent manner if a genotoxic substance such as mutagenic substance is present in the sample, then the genotoxic substance such as a mutagenic substance in the sample can be detected or measured from an amount of the luminescence.

The present method can test any genotoxic substances such as mutagenic substances. A genotoxic substance such as a mutagenic substance is usually introduced into a culture medium in form of a solution. However, solid and gas as an analyte can also be tested by the present method as far as they dissolve in a culture medium.

The luminescence can be detected or measured by a conventional method.

According to the first embodiment of the present invention, the sensitivity of detection of genotoxic substances such as mutagenic substances increases by about 100 times higher than that of the conventional method, because the sample volume required for detection in the present invention is smaller than that in the conventional method and therefore a trace amount of substances present in the environment can be detected or measured. In addition, whilst the conventional method requires at least 30 minutes for coloring reaction, the present invention immediately gives sufficient luminescence for detection, and therefore the time for detection or measurement can be shortened.

A ratio obtained by dividing a value obtained by an assay method in the presence of a genotoxic substance such as mutagenic substance by a value obtained by the same assay method in the absence of the genotoxic substance such as mutagenic substance is useful to assess a performance of the assay method.

Where 2-(2-furyl)-3-(5-nitro-2-furyl) acrylamide which is a representative mutagenic substance is measured by the present luminescence method (the first embodiment) and a conventional colorimetric method, the following result is obtained. For the conventional colorimetric method, the above defined ratio increases from 1 (when said mutagenic substance is not added) to the maximum, about 5, as the mutagenic substance increases. On the other hand, for the present luminescence method, the ratio increases from 1 (the mutagenic substance is not added) to the maximum, about 15, as the mutagenic substance increases. Accordingly, the dynamic range, i.e., the highest value of the ratio, of the present method is about 3 times wider than that of the conventional colorimetric method. This means that the present method can quantitate a genotoxic substances with higher sensitivity and higher accuracy and precision than the conventional colorimetric method.

A commonly used criterion to classify a test substance into genotoxic group or non-genotoxic group is whether or not the test substance shows a response two times higher than a response where the test substance is not added. In addition, a concentration of a test substance which exhibits a response two times higher than that wherein the test substance is not added is defined as "minimum detectable concentration". As a result of testing various genotoxic substances, minimum detectable concentration obtained by the present luminescence method are at least 4 times lower, and especially for nitroarene and polycyclic aromatic hydrocarbon about 10 times lower than those obtained by the conventional colorimetric method. This means that the sensitivity of the present luminescence method is at least 4 times higher than that of the conventional colorimetric method.

In addition, according to the second embodiment of the present invention wherein genes expressing an enzyme catalyzing the production of a substrate for luciferase is used, the steps of disruption of cells, and the addition of the substrate for luciferase are not necessary, and therefore procedures are simplified, and the time necessary for the measurement is remarkably shortened, and the cost of the reagent for detection is cut.

In addition, in the present method, the dynamic range of measurement, i.e., the highest value of the ratio, is expanded by about 10 times at maximum relative to the conventional colorimetric method, and a detectable concentration of a genotoxic substance such as a mutagenic substance is lowered by about 5 times at maximum relative to the conventional colorimetric method.

Next, the present invention is further explained in detail by Examples though the scope of the invention is not limited to the Examples.

EXAMPLE 1

Assay in *E. coli*

In the following construction of a recombinant plasmid, an umu D,C gene and luciferase gene (luc) were ligated to produce umuC-luc fusion protein. However, the production of the fusion protein is not essential as far as a gene coding for a polypeptide having luciferase activity is under the control by SOS genes.

As an SOS gene, an umu gene derived from plasmid pSK1002 having umu D,C-lacZ gene (H. Shinagawa, T.

Kato, et al., Gene, 23, 167 (1983)) was used. As a gene coding for a polypeptide having luciferase activity, a luc gene of *Photinus pyralis* on Pica Gene™ Cassette vector available from Toyo Ink MFG. Co., LTD., Japan was used.

As host strains, *E. coli* (CSH26 "Miller, J. H., Experiments in Molecular Genetics, Cold Spring Harbor Laboratory, 1972": F⁻ ara del (lac-pro)thi), and *Salmonella Typhimurium* (TA1535"Ames, B. N., J. McCann, E. Yamasaki, Mutation Res., 31, 347 (1975)": hisG46, Δgal, Δchi, Δbio, ΔuvrB, rfa⁻, SJ10002: r⁻, m⁺) were used.

A substrate solution and cell lysis reagent used for the luminescence method were of a luminescence kit "Pica Gene™" of Toyo Ink. MFG. Co., LTD. The substrate solution comprised 20 mM Tricine, 1.07 mM $(MgCO_3)_4Mg(OH)_2 19 5H_2O$, 2.67 mMMgSO$_4$, 0.1 mM EDTA, 33.3 mM DTT, 270 μM Co-enzyme A, 470 μM luciferin, and 530 μM ATP. The cell lysis reagent comprised 25 mM Tris-phosphate (pH 7.2), 2 mM DTT, 2 mM 1,2-diaminocyclohexane-N,N,N,N-tetraacetic acid, 10% glycerol, and 1% Triton X-100. A universal photon counting system manufactured by Hamamatsu Photonics Co., LTD. was used as an apparatus for measuring luminescence.

*Escherichia coli* containing pSK1002 was cultured in an LB medium (Bacto trypton 1%, Bacto yeast extract 0.5%, NaCl 1%) containing ampicillin, and a large amount of pSK1002 vector was prepared from the cells by alkaline-SDS method (Birnboim, H. C., Doly, J., *Nucl. Acids Res.*, 11, 1513 (1979)). The vector was digested with restriction enzymes HindIII and AvaI to obtain DNA fragment (A) of about 7.2 Kb containing an umu gene. The fragment (A) was dephosphorylated with alkaline phosphatase (*E. coli* C75).

A vector containing a luc gene derived from *Photinus pyralis* was used to transform *E. coli* JM109 (Messing, J., Gene, 33, 199 (1985)). The transformed *E. coli* was cultured in LB medium containing ampicillin, and a large amount of vector containing luc gene was prepared by alkaline SDS method. The vector was digested with restriction enzymes HindIII and StuI to obtain a DNA fragment (B) of about 1.7 Kb containing luc gene.

After the fragments (A) and (B) were ligated using a DNA Ligation Kit (Takara Shuzo), the resulting fragment was digested with restriction enzyme stuI, and blunt-ended using DAN blunting kit (Takara Shuzo), and self-ligated using a DNA Ligation Kit so as to construct an expression vector.

For the production of umuC-luc fusion protein, the expression vector constructed above was digested with a restriction enzyme HindIII, blunt-ended by a DNA Blunting Kit, and self-ligated using a DNA Ligation Kit so as to construct umuC-luc fusion protein-producing luminescence vector.

*E. coli* CSH26 was cultured in an LB medium overnight. To the LB medium was added one hundredth volume of the culture broth, and cultivation was carried out until the turbidity at 600 nm ($OD_{600}$) reached about 0.4. Next, 5 ml of the culture broth was centrifuged, the precipitate fraction (microbial cells) was suspended in 5 ml of 30 mM CaCl$_2$, and the suspension was allowed to stand for 45 minutes in an ice bath. Centrifugation was again carried out and the cells were suspended in 0.4 ml of 30 mM CaCl$_2$.

To 100 μl of competent cells of *E. coli* CSH26 thus prepared, was added about 200 ng of the luminescence vector, and the mixture was allowed to stand for 30 minutes in an ice bath. After treatment at 42° C. for 2 minutes, the mixture was allowed to stand for 5 minutes at room temperature. One ml of LB medium was added thereon, and the mixture was incubated at 37° C. for one hour. This mixture was inoculated on an LB plate containing 50 μg/ml ampicillin.

*E. coli* CSH26 cells transformed with a luminescence vector were cultured in an LB medium containing ampicillin 20 μg/ml. The culture broth was inoculated into an LB medium at a 1/50 volume of the medium, and cells were cultured at 37° C. until logarhysmic growth phase ($OD_{600}$= 0.2 to 0.3). 29 μl of the culture broth was distributed into test tubes and to each tube was added 1 μl of 2-(2-furyl)-3-(5-nitro-2-furyl)-acrylamide (AF-2) having a predetermined concentration, and the mixture was incubated at 37° C. for 2 hours.

The cell suspension was centrifuged, and to the precipitate (cells) was added 20 μl of the cell lysis reagent. The suspension was treated with ultrosonic disruption apparatus (Tosho Denki) five times for 30 seconds, and the suspension was centrifuged. To 10 μl of the supernatant, 100 μl of a luminescence substrate was added, and luminescence was measured. The photon number in 8.192 seconds (2 mill seconds×4096 times) was counted so as to obtain luciferase activity. A result is shown in FIG. 1.

EXAMPLE 2

Assay in Salmonella (TA1535)

According to the same procedure as described in Example 1, competent cells of *S. typhimurium* SJ10002 were prepared. *S. typhimurium* TA1535 was cultured in LB medium overnight. The culture broth was added to a fresh LB medium in an amount of one hundredth relative to the fresh medium, and cultured until a turbidity at 600 nm ($OD_{600}$) reached to about 0.4. 5 ml of the culture broth was centrifuged, the precipitate (microbial cells) was suspended in 5 ml of 10 mM CaCl$_2$, 10 mMMnCl$_2$, 10 mMMgCl$_2$ aqueous solution, and the mixture was allowed to stand for 45 minutes in an ice bath. The mixture was again centrifuged, the cells were suspended in 0.4 ml of 10 mM CaCl$_2$, 10 mMMnCl$_2$, 10 mM MgCl$_2$ aqueous solution so as to prepare competent cells.

To 100 μl of the competent cells of *S. typhimurium* SJ10002 was added about 200 ng of the luminescence vector (prepared in Example 1), and the mixture was allowed to stand for 30 minutes in an ice bath. After treatment for 2 minutes at 42° C., the mixture was allowed to stand for 5 minutes at room temperature. After adding 1 ml of LB medium, the mixture was incubated at 37° C. for one hour. This suspension was inoculated on LB plate containing 50 μg/ml of ampicillin.

Luminescence vector was prepared from transformed *S. typhimurium* SJ10002 by alkaline-SDS method, and the vector was used to transform *S. typhimurium* TA1535 according to the same procedure as described above.

Figure 2:
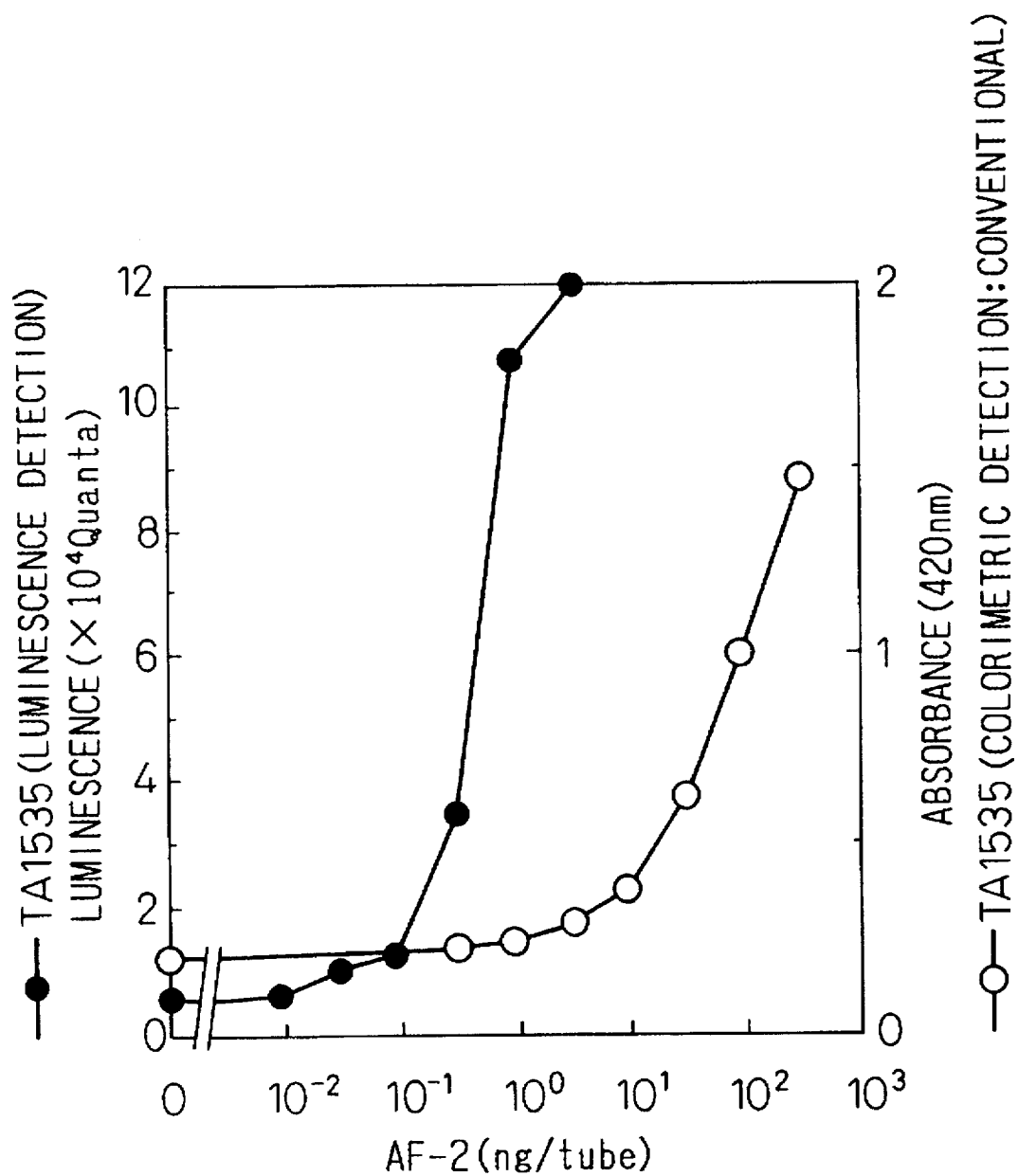
FIG. 2 shows a result of luminescence measurement method obtained in Example 2 (solid circles) and of colorimetric method obtained in Comparative Example 2 (open circles).

Using *S. typhimurium* TA1535 transformed with the luminescence vector, measurement of luminescence by the addition of AF-2 was carried out according to a procedure similar to that in Example 1 using TGA medium (Trypton 1%, NaC10.5%, glucose 0.2%, ampicillin 20 μg/ml) in place of LB medium. A result is shown in FIG. 2.

The following Comparative Examples were carried out in order to compare the present method with the conventional method.

Comparative Example 1

*E. coli* CSH26/pSK1002 in which plasmid pSK1002 had been introduced was used. 0.75g of potassium chloride, 0.246 g of magnesium sulfate, and 2 ml of 0.05 mol/L 2-mercaptoethanol were added to 1 L of 0.1 mol/L potassium phosphate buffer (pH 7.0) to prepare Z-Buffer.

*E. coli* CSH26/pSK1002 was cultured in LB medium containing 20 µg/ml ampicillin overnight. The culture broth was inoculated to the same medium in an amount of 1/50 volume ratio relative to the medium, and cultured at 37° C. until logarithmic growth phase ($OD_{600}$=0.2 to 0.3). 2.9 ml of the culture broth was distributed to each test tube, and after adding 0.1 ml of AF-2 having a predetermined concentration thereon, the mixture was incubated at 37° C. for 2 hours. To 0.2 ml of the culture broth were added 1.8 ml of Z-Buffer, 50 µl of 0.1% SDS and 10 µl of chloroform, and the mixture was stirred for 5 seconds. Next, 0.4 ml of 4 mg/ml o-nitrophenyl-β-D-galactopyranoside (ONPG) aqueous solution in 0.1M phosphate buffer (pH 7.0) was added, and after reaction at 28° C. for 10 minutes, the reaction was terminated by adding 1 ml of 1 mol/L sodium carbonate solution. After the termination of the reaction, absorbance at 420 nm was measured. A result is shown in FIG. 1.

Comparative Example 2

*Salmonella typhimurium* TA1535/pSK1002 into which plasmid pSK1002 had been introduced was used, and the same procedure as described in Comparative Example 1 was repeated except that TGA medium (Trypton 1%, $NaCl_{0.5}$%, glucose 0.2%, ampicillin 20 µg/ml) was used in place of LB medium to measure β-galactosidase activity induced by AF-2. A result is shown in FIG. 2.

As shown in FIGS. 1 and 2, *E. coli* CSH26 carrying a recombinant plasmid containing a luminescence gene provided a good dose-response curve over a range of about 1 ng/tube to about 10 ng/tube of AF-2. *S. typhimurium* TA1535 carrying a recombinant plasmid containing a luminescence gene provided a good dose-response curve over a range of about 0.1 ng/tube to 1 ng/tube.

In comparison with conventional methods (Comparative Examples), for both the strains *E. coli* CSH26 and *S. typhimurium* TA1535, the sensitivity of the present method is higher about 100 times relative to that of the conventional method.

EXAMPLE 3

Assay in Salmonella (TA1535) Metabolic activation enzyme

An S9 fraction (manufactured by Oriental Yeast) derived from the rat liver, which was treated with phenobarbital and 5,6-benzoflavone, was used, and S9Mix which was prepared by adding Cofactor-1 (manufactured by Oriental Yeast) as a co-factor was used.

Test sample

AF-2, 4-nitroquinoline 1-oxide (4NQO), 1-nitropyrene (1-NP), 2-aminoanthracene (2-AA) and benzo[a]pyrene (BaP) were used as test samples.

The *S. typhimurium* TA1535 transformed with a luminescence vector, obtained in Example 2, was cultured in TGA medium at 37° C. overnight. The culture broth was inoculated to a fresh TGA medium in an amount of 1/50 volume ratio relative to the fresh medium, and cultured at 37° C. for 1.5 hours. The resulting culture broth was diluted with TGA medium so that an absorbance at 600 nm was 0.1. 1.45 ml of the diluted culture broth was distributed to each test tube, and to the diluted culture broth was added 50 µl of a test sample having a predetermined concentration and cultivation was carried out at 37° C. for 2 hours. In the case where a metabolic activation enzyme is necessary, to 1.2 ml of the diluted culture were added 0.25 ml of S9Mix and 50 µl of a test sample, and cultivation was carried out at 37° C. for 2 hours.

Figure 3:
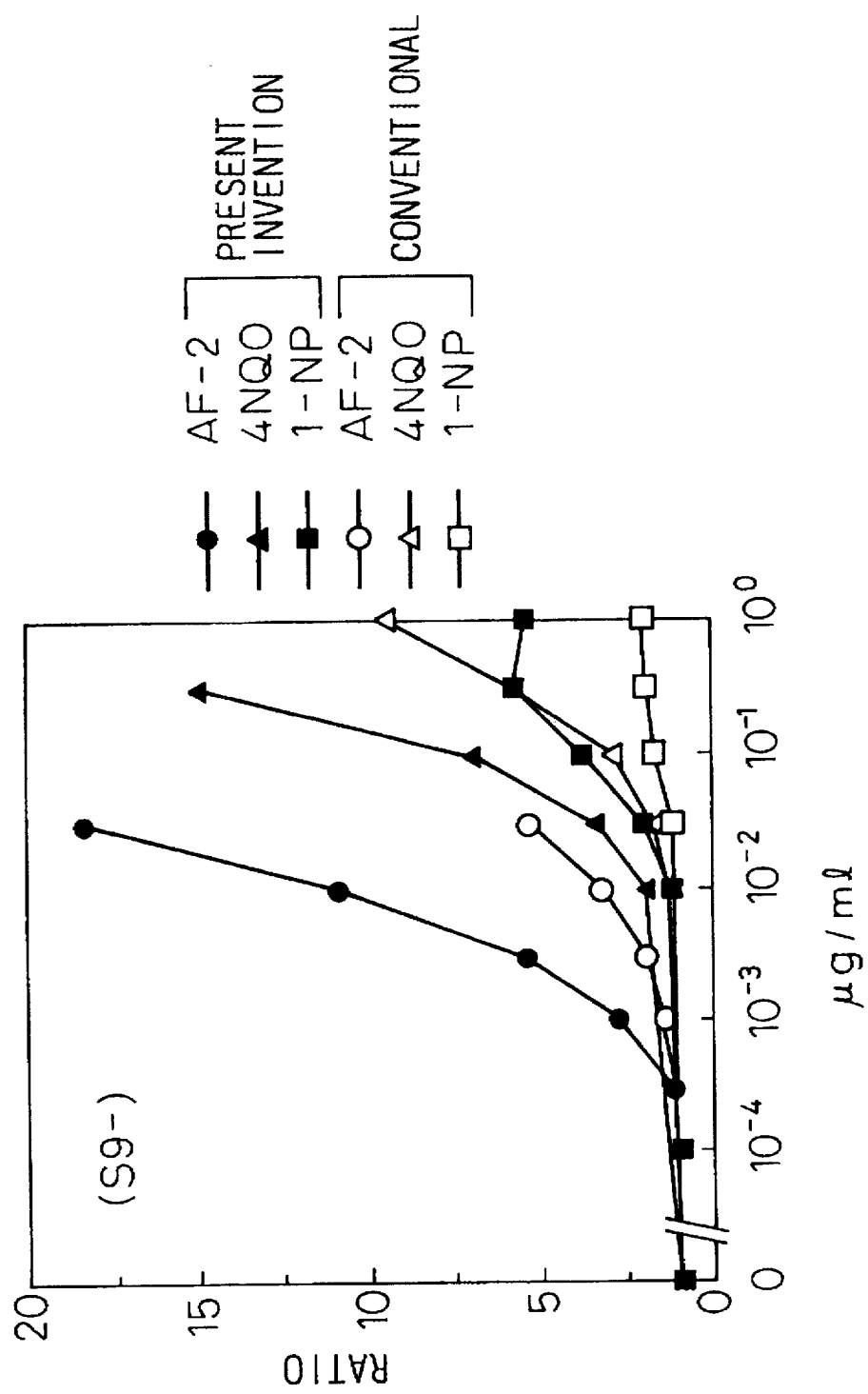
FIG. 3 is a graph wherein a ratio (0 to 20) obtained by dividing responses at different concentration of samples by response at sample-free Condition are plotted against concentrations of the samples. The values were obtained in Example 3 and Comparative Example 3.
Figure 4:
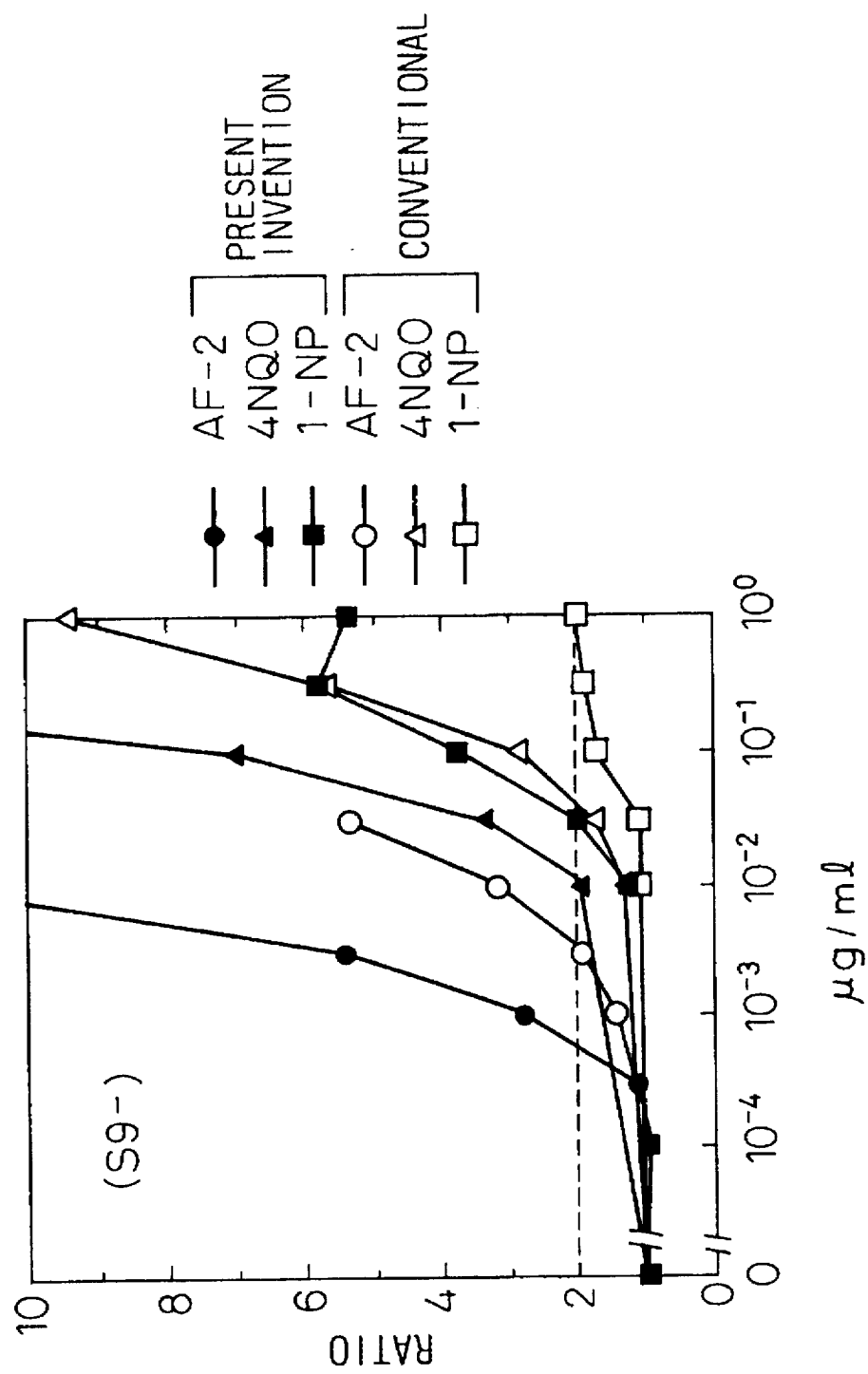
FIGS. 4 and 5 are graphs wherein a ratio (0 to 10) obtained by dividing responses at different concentrations of samples by response at sample-free condition are plotted against concentrations of the samples. The values were obtained in Example 3 and Comparative Example 3.
Figure 5:
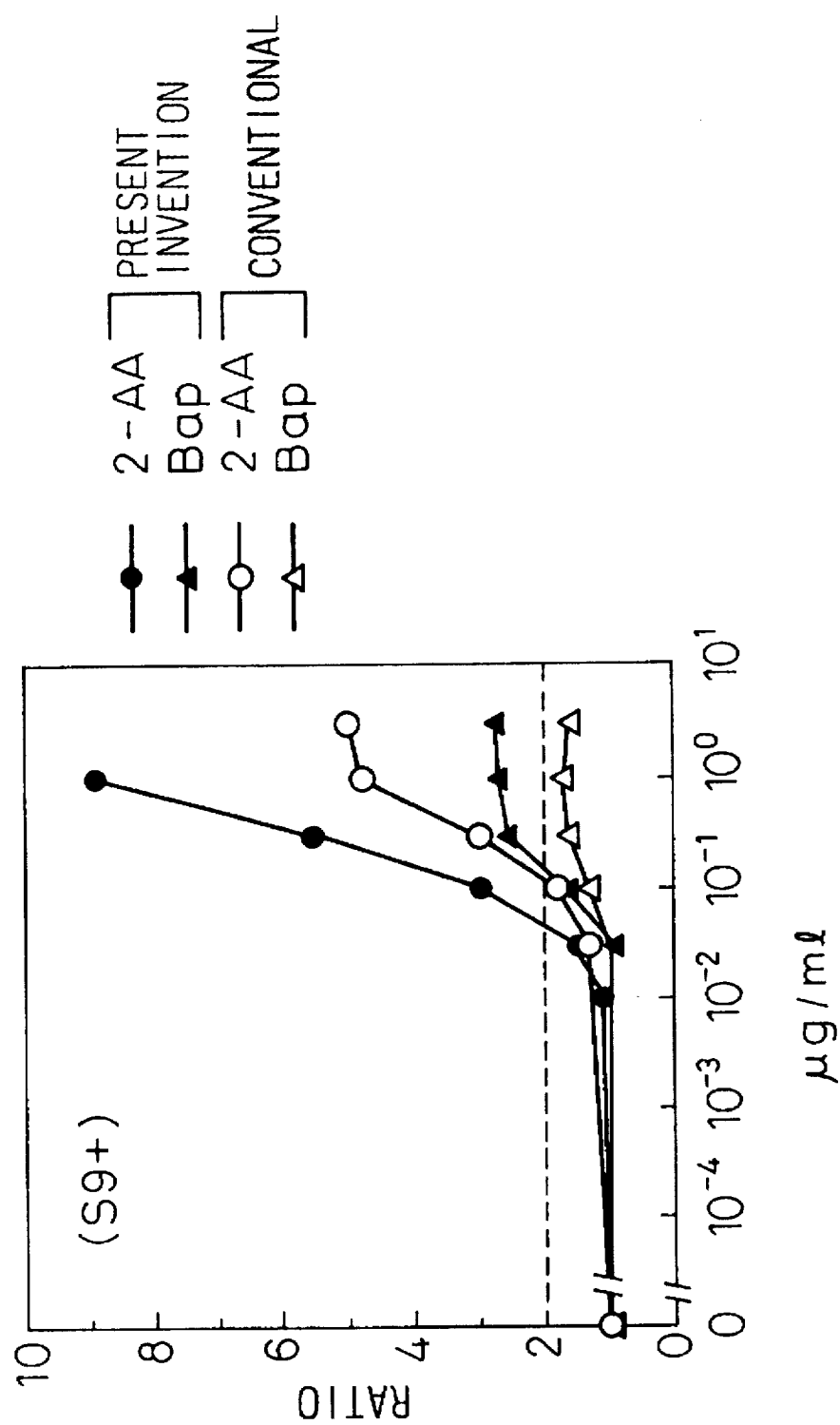

After the cultivation, 0.5 ml of the culture broth was centrifuged, and to the precipitated fraction (microbial cells) was added 50 µl of cell lysis reagent to prepare a suspension. 10 µl of the suspension and 100 µl of a luminescence substrate were added to a 96-well microplate for microluminoreader, and an amount of the luminescence was measured by a luminometer (Miroluminoreader MLR-100 manufactured by Corona). In addition, $OD_{600}$ of the culture broth was measured. An activity (Intensity/$OD_{600}$) was obtained by dividing an amount of the luminescence for 10 seconds by $OD_{600}$. A result is shown in FIGS. 3 to 5.

Comparative Example 3

*S. typhimurium* TA1535/pSK1002 was cultured in TGA medium at 37° C. overnight. The culture broth was inoculated to a fresh TGA medium in a volume ratio of 1/50 relative to the fresh medium, and cultured at 37° C. for 1.5 hours. The resulting culture broth was diluted with TGA medium so that an absorbance at 600 run was 0.1. 1.45 ml of the diluted culture broth was distributed to each test tube, and to the diluted culture broth was added 50 µl of a test sample having a predetermined concentration and cultivation was carried out at 37° C. for 2 hours. In the case where a metabolic activation enzyme is necessary, to 1.2 ml of the diluted culture were added 0.25 ml of S9 Mix and 50 µl of a test sample, and cultivation was carried out at 37° C. for 2 hours. $OD_{600}$ of the culture broth was measured. To 0.1 ml of the remaining culture broth were added 0.9 ml of Z-Buffer, 50 µl of 0.1% SDS and 10 µl of chloroform and the mixture was stirred for 5 seconds. Next, 0.2 ml of 4 mg/ml ONPG aqueous solution dissolved in 0.1M phosphate buffer (pH 7.0) was added, and after reaction at 28° C. for 10 minutes, the reaction was terminated by adding 0.5 ml of 1 mol/L sodium carbonate solution. After the termination of the reaction, absorbances were measured at 420 nm and 550 nm. An activity (unit) was calculated by Miller's method according to the following equation.

$$\text{Activity} = 1000 \times \frac{(OD_{420} - 1.75 \times OD_{550})}{OD_{600}}$$

As shown in FIGS. 3 and 5, the present luminescence measuring method provided a dynamic range of the measurement, i.e., the highest value of the ratio, which is expanded few times in comparison with that of conventional colorimetric method for each test sample.

As shown in FIGS. 4 and 5 as well as in Table 1, in the present luminescence measuring method, a minimum detectable concentration lowered by at least about times in comparison with the conventional colorimetric method for each test sample. Especially, for nitroarene (1-NP) and polycyclic aromatic hydrocarbon (BaP), a minimum detectable concentration lowered by about 10 times.

TABLE 1

| | Minimum detectable concentration (µg/ml) | |
|---|---|---|
| Test Sample | Method of Present Invention | Conventional Method |
| AF-2 | $5 \times 10^{-4}$ | $3 \times 10^{-3}$ |
| 4NQO | $1 \times 10^{-2}$ | $4 \times 10^{-2}$ |
| 1-NP | $3 \times 10^{-2}$ | $3 \times 10^{-1}$ |
| 2-AA | $4 \times 10^{-2}$ | $1 \times 10^{-1}$ |
| Bap | $1 \times 10^{-1}$ | 1 |

The following Example was carried out to clarify the mechanism for expansion of dynamic range and lowering a minimum detectable concentration.

EXAMPLE 4

A predetermined amount of luciferase dissolved in 10 μl of cell lysis reagent, and 100 μl of a luminescence substrate were added to a 96-well microplate for microluminoreader, and an amount of luminescence for 10 seconds was measured. A result is shown in FIG. 6 wherein an amount of enzyme (luciferase) is plotted on the horizontal axis, and a corresponding activity (an amount of luminescence) is plotted on the vertical axis.

0.9 ml of Z-Buffer, 50 μl of 0.1% SDS and 10 μl of chloroform were added to β-galactosidase dissolved in 0.1 ml of water, and the mixture was stirred for seconds. Next, 0.2 ml of 4 mg/ml ONPG aqueous solution in 0.1 M phosphate buffer (pH 7.0) was added thereon, after reaction at 28° C. for 10 minutes, 0.5 ml of 1 mol/L sodium carbonate solution was added to terminate the reaction. After the termination of the reaction, an absorbance at 420 nm was measured. A β-galactosidase activity (unit) was calculated according to the following equation.

Activity=1000×OD$_{420}$

Figure 6:
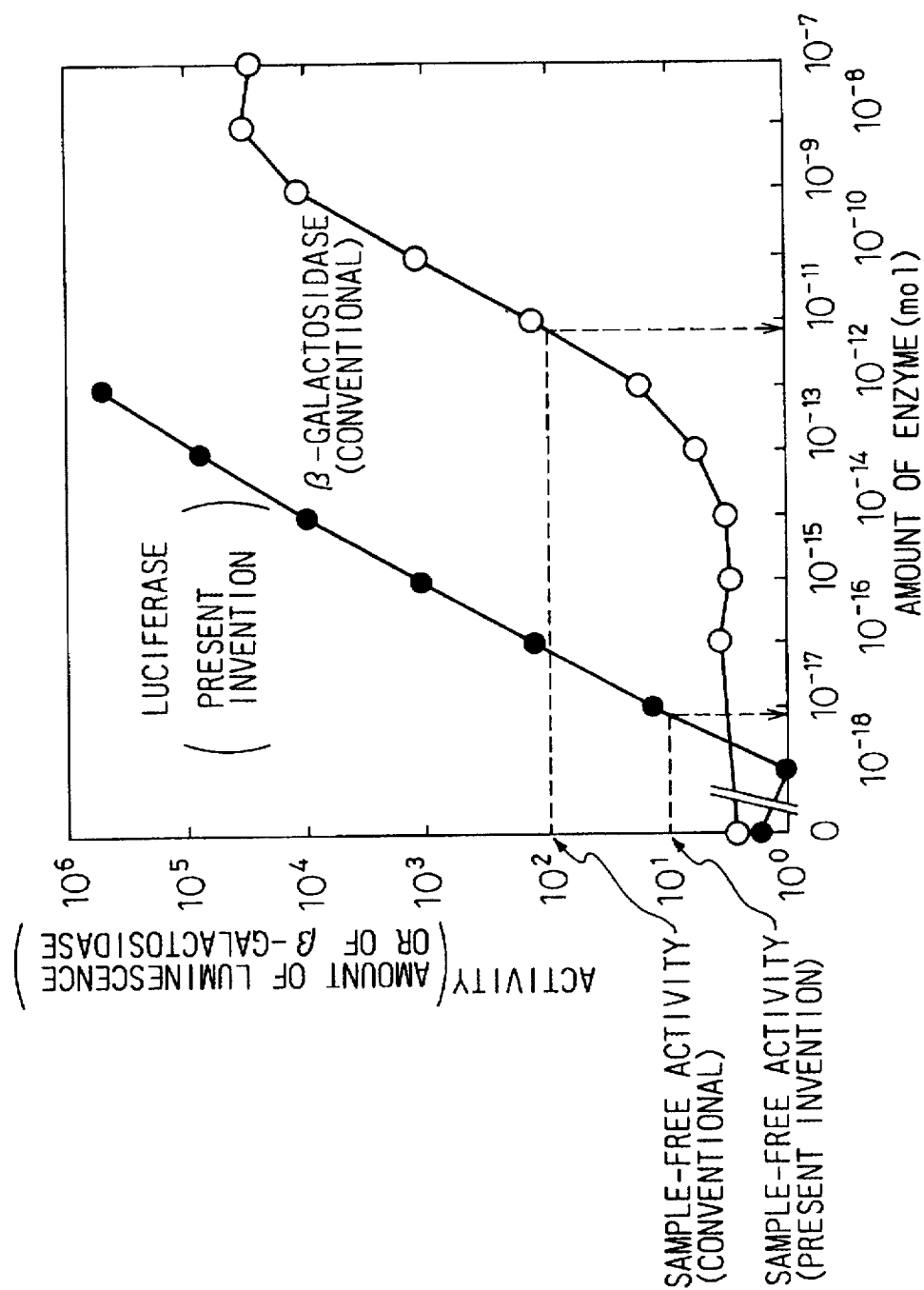
FIG. 6 shows lines showing the relationship between an amount of luciferase or β-galactosidase and its activity, obtained in Example 4.

A result is shown in FIG. 6 wherein an amount of enzyme (an amount of β-galactosidase) is plotted on the horizontal axis, and an activity (β-galuctosidase activity) is plotted on the vertical axis.

Figure 7:
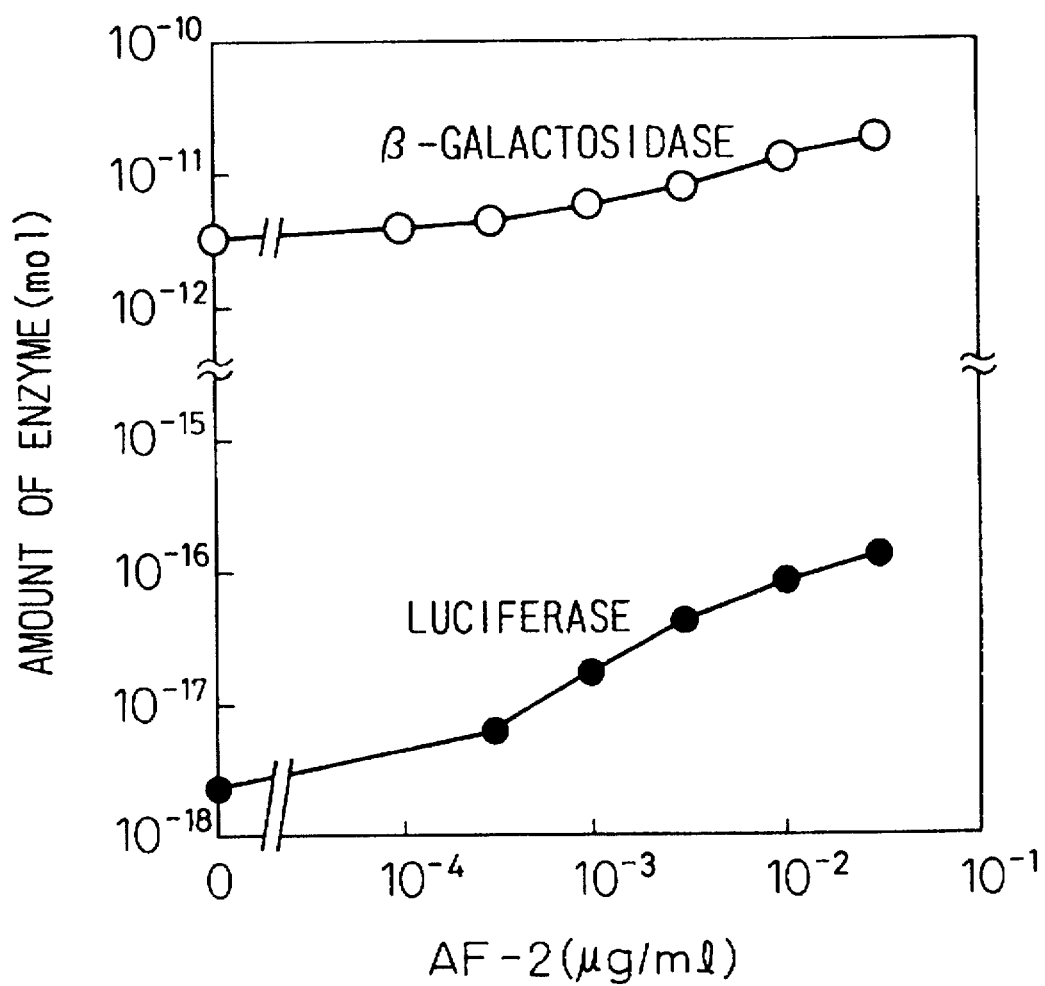
FIG. 7 is a graph wherein amounts of luciferase or β-galactosidase induced by the addition of different concentrations of AF-2 are plotted against the concentrations of AF-2. The amounts of luciferase and β-galactosidase were calculated using the lines in Example 4.

In addition, amounts of enzymes (luciferase and β-galactosidase) induced by AF-2 of different concentrations were calculated from Example 3, Comparative Example 3 and FIG. 6. A result is shown in FIG. 7.

From the result of FIGS. 6 and 7, the reason of high sensitivity of the present method can be speculated as follows.

An expression efficiency of luciferase is totally lower than that of β-galactosidase, and therefore in the case where a test sample is not added, luciferase is expressed only about 1/10$^6$ of β-galactosidase. Namely, a large amount of β-galactosidase is synthesized even when a test sample is not added. Probably under the influence of this phenomenon, response in induction of synthesis of β-galactosidase is slow, and a relative ratio of an amount of β-galactosidase produced by induction by a test sample to an amount of β-galactosidase produced without induction is small. On the other hand, response in induction of synthesis of luciferase is faster, and a relative ratio of an amount of luciferase produced by induction by a test sample to an amount of luciferase produced without induction is larger. The rapid response of luciferase gene in induction of synthesis of luciferase by the addition of a test sample means that a minimum detectable concentration is low, and the high ratio of an amount of luciferase synthesized by induction to an amount of luciferase synthesized without induction means that the dynamic range of a measurement, i.e., the highest value of the ratio, is wide.

The above-mentioned phenomena and the advantages of the present invention are provided by the difference in expression of β-galactosidase gene and luciferase gene in the host strain *Salmonella typhimurium* TA1535, and are found, for the first time, by detailed research in the present invention. In addition, the low expression efficiency of reporter gene means that detection by conventional colorimetric method is difficult, and the present invention is characterized by, and the advantages thereof are provided by, the use of luciferase gene and measurement of the luminescence.

EXAMPLE 5

Construction of luminescence vector and preparation of transformant

As an SOS gene, umu D,C gene in plasmid pSK1002 introduced in *E. coli* (CSH26 "Miller, J. H., Experiments in Molecular Genetics, Cold Spring Harbor Laboratory, 1972": F$^-$ ara del (lac-pro) thi) was used. As a gene expressing luciferase activity and an enzyme which catalyze the production of a substrate for the enzyme, a group of luminescence genes in plasmid pUCD620 (Clarence I. Kado et al., Plant Molecular Biology Reporter, 5, 225 (1987)) introduced in *E. coli* (HB101: hsd20 (r$_B^-$, m$_B^-$), recA13, ara-14, proA2, lacY1, galK2, rpsL20, xyl-5, mtl-1, supE44) was used.

As a host microorganism, *Salmonella typhimurium* (TA1535, "Ames, B. N., J. McCann, E. Yamasaki, Mutation Res., 31, 347, 1975": hisG46, Δgal, Δchl, Δbio, ΔuvrB, rfa$^-$, SJ10002: r$^-$, m$^+$) was used.

Microluminoreader MLR-100 manufactured by Colona was used for the measurement of luminescence.

*E. coli* CSH26 carrying the plasmid pSK1002 was cultured in LB medium (Bacto Trypton 1%, Bacto yeast extract 0.5%, NaCl 1%) containing ampicillin, and a large amount of the plasmid pSK1002 was prepared from the cultured cells by an alkaline extraction method described in Birnboim, H. C., Doly, J., Nucl. Acids Res., 11, 1513, 1976. The plasmid pSK1002 was digested with SalI and SmaI to obtain a SalI-SmaI DNA fragment of about 7.5 kb containing a umu D,C gene. This DNA fragment was ligated with T4 DNA ligase, and used to transform *E. coli* DH5 according to a conventional procedure.

From the transformant thus obtained, plasmid was isolated by alkaline extraction method. The plasmid was digested with MluI, and blunt-ended with T4 DNA polymerase. A DNA linker (TAGGATCCTA) (SEQ.ID NO:1) which provides a stop codon to the umuC and has BamHI restriction site was chemically synthesized. This synthetic linker and said MluI DNA fragment were ligated with T4 DNA ligase, and the product was used to transform *E. coli* DH5. From the resulting transformant, the plasmid was extracted by alkaline extraction method. The plasmid was digested with BamHI and SalI to obtain a BamHI-SalI DNA fragment of about 7.4 kb.

*E. coli* HB101 carrying plasmid pUCD620 was cultured in LB medium containing ampicillin and a large amount of pUCD620 was prepared from the cultured cells by alkaline extraction method. The plasmid pUCD620 was digested with BamHI and SalI to obtain a BamHI-SalI DNA fragment of about 7.5 kb containing a group of luminescence genes. This DNA fragment was ligated to the downstream of said BamHI-SalI DNA fragment of about 7.4 kb with T4 DNA ligase to construct a luminescence vector.

*S. typhimurium* SJ10002 was cultured in LB medium overnight. The culture broth was inoculated to a fresh LB medium in an amount of one hundredth volume of the fresh medium, and was cultured until a turbidity at 600 nm (OD$_{600}$) reached about 0.4. 5 ml of the culture broth was centrifuged, and the precipitated fraction was suspended in 5 ml of 30 mM CaCl$_2$, and the suspension was allowed to stand for 45 minutes in an ice bath. The suspension was again centrifuged, and the precipitated cells were suspended in 0.4 ml of 30 mM CaCl$_2$ aqueous solution to prepare competent cells of *S. typhimurium* SJ10002.

*S. typhimurium* TA1535 was cultured in LB medium overnight. The culture broth was inoculated to a fresh LB medium in an amount of one hundredth by volume of the fresh medium, and cultured until a turbidity at 600 nm (OD$_{600}$) reached about 0.4. 5 ml of the culture was centrifuged, and the precipitated fraction was suspended in 5 ml of 10 mM $CaCl_2$, 10 mM $MnCl_2$, 10 mM $MgCl_2$ aqueous solution, and the mixture was allowed to stand for 45 minutes in an ice bath. The suspension was again centrifuged, and the precipitated cells were suspended in 0.4 ml of 10 mM $CaCl_2$, 10 mM $MuCl_2$ 10 mMMg aqueous solution to prepare competent cells of S. typhimurium TA1535.

About 200 ng of the luminescence vector was added to 100 μl of the competent cells of S. typhimurium SJ10002, and the suspension was allowed to stand for 30 minutes in an ice bath. After the treatment at 42° C. for 2 minutes, the suspension was allowed to stand for 5 minutes at room temperature. 1 ml of LB medium was added thereon, and the suspension was incubated at 37° C. for one hour, and inoculated to an LB plate containing 50 μg/ml ampicillin.

From the transformed S. typhimurium SJ10002 thus obtained, the luminescence vector was prepared by alkaline extraction method and used to transform S. typhimurium TA1535 as described above.

EXAMPLE 6

Luminescence assay
Metabolic activation enzyme

An S9 fraction (manufactured by Oriental Yeast) derived from the rat liver, which was treated with phenobarbital and 5,6-benzofluvone, was used, and S9 Mix which was prepared by adding Cofactor i (manufactured by Oriental Yeast) as a co-factor was used.

Test sample 2-(2-Furyl)-3-(5-nitro-2-furyl)acrylamide (AF-2), 4-nitroquinoline 4-oxide (4NQO), 1-nitropyrene (1-NP), 2-aminoanthracene (2-AA) and benzo[a]pyrene (Bap) were used.

S. typhimurium TA1535 transformed with a 5 luminescence vector was cultured in TGA medium (Trypton 1%, NaCl 0.5%, glucose 0.2%, ampicillin 20 μg/ml) at 30° C. overnight. The culture broth was inoculated to a fresh TGA medium in an amount of 1/50 by volume of the fresh medium, and cultured at 30° C. for 1.5 hours. The culture broth was diluted with TGA medium so that absorbance at 600 rim was 0.1. 1.45 ml of the diluted culture broth was distributed to each test tube, and to the diluted culture broth was added 50 μl of a test sample having a predetermined concentration, and cultivation was carried out at 30° C. for 2 hours. In the case where a metabolic activation enzyme was necessary, to 1.2 ml of the diluted culture broth were added 0.25 ml of S9 Mix and 50 μl of a test sample, and cultivation was carried out at 30° C. for 2 hours. Immediately after the cultivation an amount of luminescence of 100 μl of the culture broth was measured by a luminometer. In addition, $OD_{600}$ of the culture broth was also measured. An activity (Intensity/$OD_{600}$) was obtained by dividing an amount of the luminescence for 10 seconds by $OD_{600}$. A result is shown in FIGS. 8 to 11.

The following Comparative Example was carried out to compare the sensitivity of the present method and that of the conventional method.

Comparative Example 4

Salmonella typhimurium TA1535/pSK1002 into which plasmid pSK1002 had been introduced was used. 0.75 g of potassium chloride, 0.246 g of magnesium sulfate and 2 ml of 0.05 mol/L 2-mercaptoethanol were added to 1L of 0.1 mol/L potassium phosphate buffer (pH 7.0) to prepare Z-Buffer.

The TA1535/pSK1002 was cultured in TGA medium at 37° C. overnight. The culture broth was inoculated to a fresh TGA medium in an amount of 1/50 by volume of the fresh medium, and cultured at 37° C. for 1.5 hours. The culture broth was diluted with TGA medium so that an absorbance at 600 nm was 0.1. 1.45 ml of the diluted culture broth was distributed to each test tube, 50 μl of 5 a test sample having a predetermined concentration was added thereon, and cultivation was carried out at 37° C. for 2 hours. In the case where a metabolic activation enzyme is necessary, to 1.2 ml of the diluted culture broth were added 0.25 ml of S9 Mix, and 50 μl of a test sample, and cultivation was carried out at 37° C. for 2 hours. $OD_{600}$ of the culture broth was measured.

To 0.1 ml of the remaining culture broth were added 0.9 ml of Z-Buffer, 50 μl of 0.1% SDS and 10 μl of chloroform, and the mixture was stirred for 5 seconds. Next, 0.2 ml of 4 mg/ml o-nitrophenyl-β-D-galactopyranoside (ONPG) dissolved in 0.1M phosphate buffer (pH 7.0) was added thereon, and after reaction at 28° C. for 10 minutes, the reaction was terminated by adding 0.5 ml of 1 mol/L sodium carbonate. Next, after the termination of the reaction, absorbances at 420 nm and 550 nm were measured. An activity (unit) was calculated by Miller's method according to the following equation.

$$Activity = \frac{COD_{420} - 1.75 \times OD_{550}}{OD_{600}}$$

Figure 8:
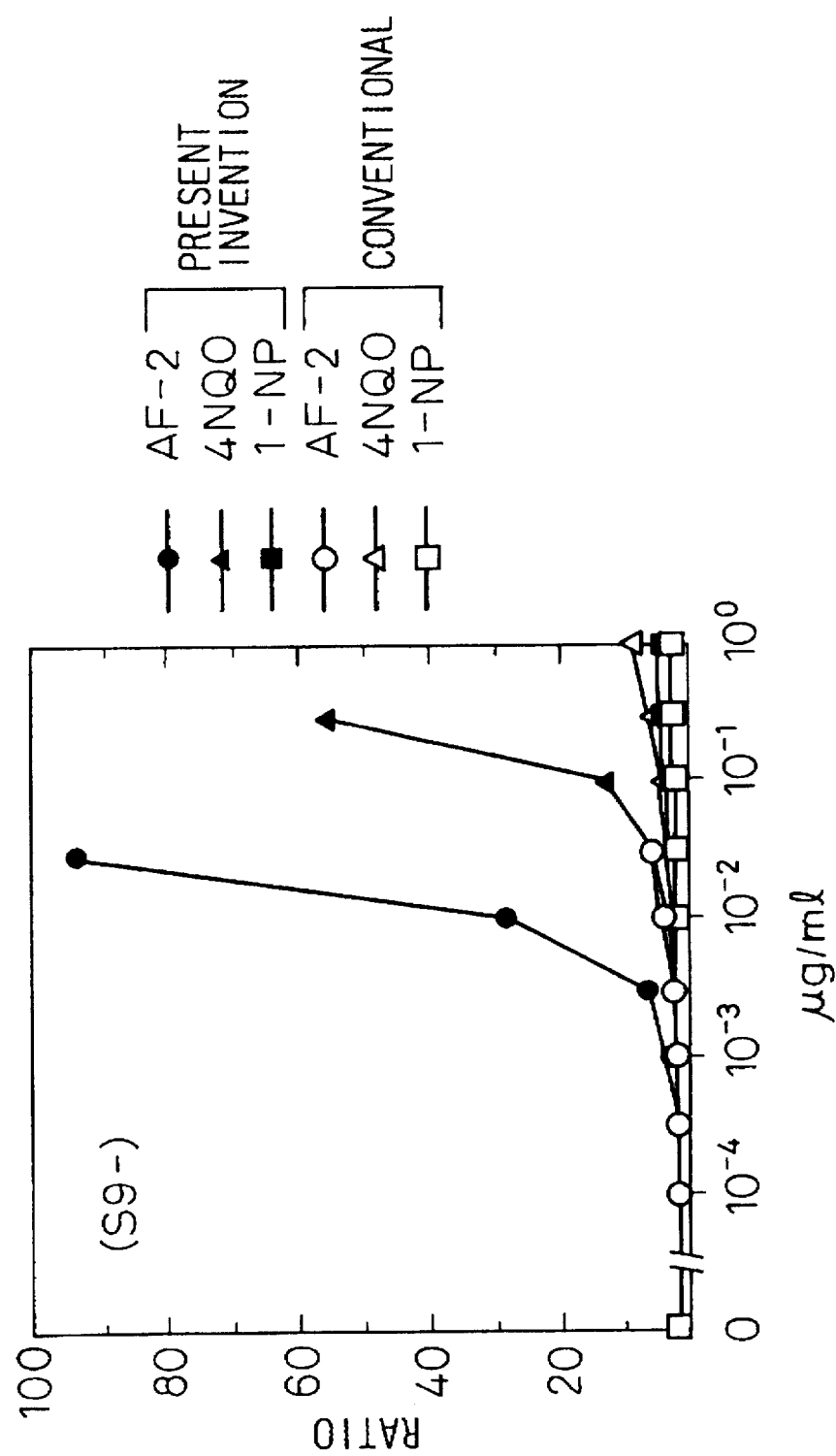
FIG. 8 is a graph showing a ratio (0 to 100) obtained by dividing response obtained in Example 6 and Comparative Example 4 for AF-2, 4NQO and 1-NP at different concentrations, by response at sample-free condition.

As shown in FIGS. 8 and 10, the present luminescence measuring method provided a dynamic range of a measurement, i.e., the highest value of the ratio, expanded by about 10 times at maximum.

Figure 9:
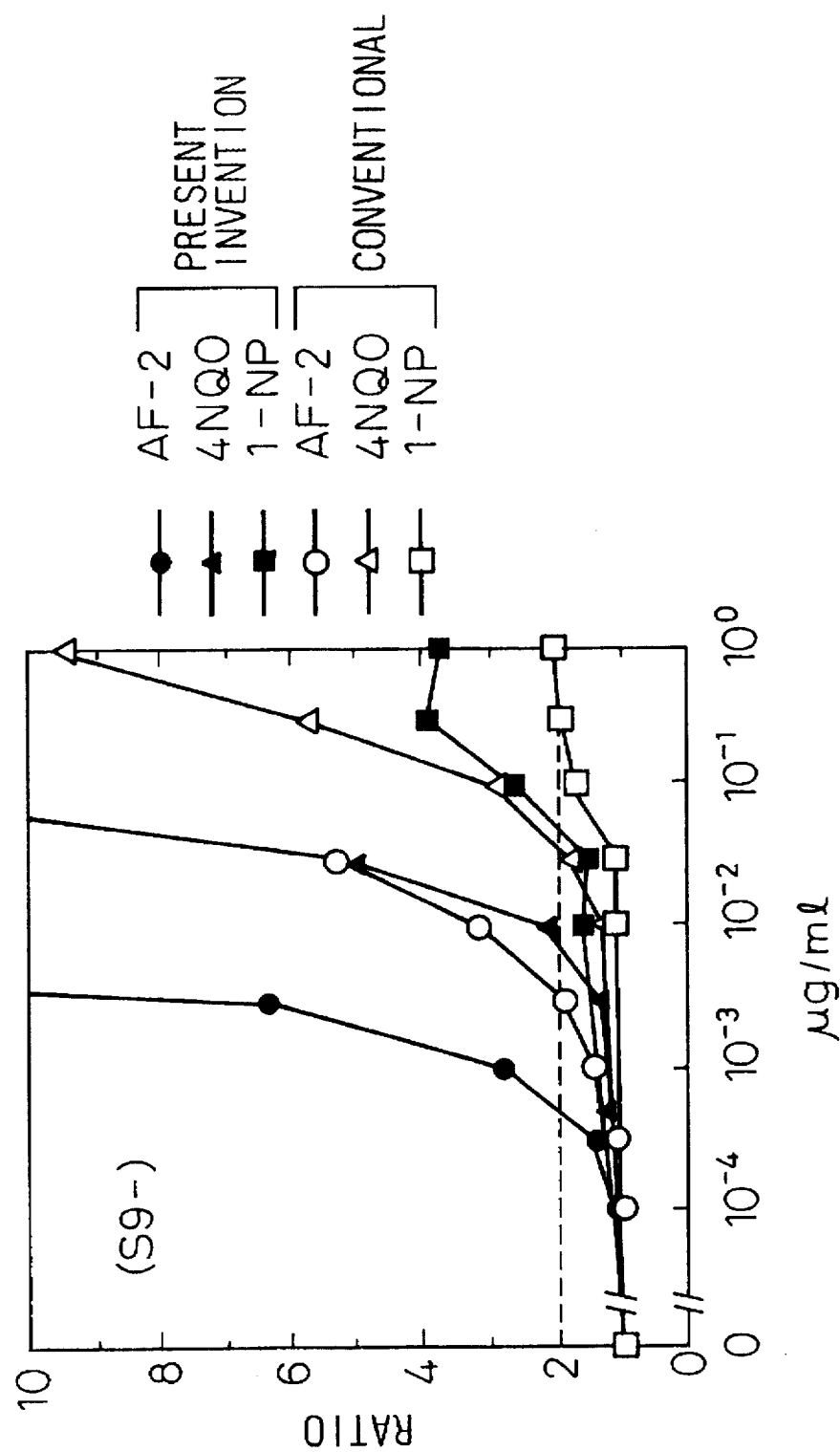
FIG. 9 is a graph showing ratio (0 to 10) obtained by dividing responses obtained in Example 6 and Comparative Example 4 for AF-2, 4NQO and 1-NP at different concentrations, by response at sample-free condition.

As shown in FIGS. 9 and 11, as well as Table 2, in the present luminescence measuring method, minimum detectable concentration lowered by at least 5 times in comparison with the conventional colorimetric method.

TABLE 2

| | Minimum detectable concentration (μg/ml) | |
|---|---|---|
| Test Sample | Method of Present Invention | Conventional Method |
| AF-2 | $5 \times 10^{-4}$ | $3 \times 10^{-3}$ |
| 4NQO | $8 \times 10^{-3}$ | $4 \times 10^{-2}$ |
| 1-NP | $5 \times 10^{-2}$ | $3 \times 10^{-1}$ |
| 2-AA | $2 \times 10^{-2}$ | $1 \times 10^{-1}$ |
| Bap | $4 \times 10^{-2}$ | 1 |

We claim:

1. A method for identifying a mutagenic substance, comprising the steps of: culturing Escherichia or Salmonella transformed with recombinant DNA comprising (i) an scherichia or Salmonella SOS gene and (ii) a gene encoding luciferase isolated from *Photobacterium phosphoreum, Photobacterium leiognethi, Vibrio splendidus, Vibrio cholerae, Photinus pyralis, Vibrio harveyi* or *Vibrio fischeria*;

wherein said gene encoding luciferase is positioned downstream of said SOS gene such that when said SOS gene is expressed, then said gene encoding luciferase is also expressed;

contacting said culture with a substance to be tested wherein said Escherichia or Salmonella in said culture is provided with a luciferase substrate; and determining whether said substance is mutagenic by measuring the amount of luminescence in said culture.

2. The method of claim 1, wherein said method comprises collecting and disrupting said cultured Escherichia or salmonella to release luciferase therefrom and providing said luciferase substrate to said released luciferase.

3. The method of claim 1, wherein, when said luciferase gene is isolated from *Photobacterium leiognethi, Vibrio splendidus, Vibrio cholerase, Vibrio harveyi* or *Vibrio fischeria*, said recombinant DNA further comprises luciferase operon genes encoding a fatty acid reductase, positioned downstream from said SOS gene, so that when said SOS gene is expressed, said fatty acid reductase genes are expressed.

\* \* \* \* \*